US006426991B1

(12) United States Patent
Mattson et al.

(10) Patent No.: US 6,426,991 B1
(45) Date of Patent: Jul. 30, 2002

(54) BACK-ILLUMINATED PHOTODIODES FOR COMPUTED TOMOGRAPHY DETECTORS

(75) Inventors: Rodney A. Mattson, Mentor; Chris J. Vrettos, Willoughby, both of OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/714,685

(22) Filed: Nov. 16, 2000

(51) Int. Cl.[7] .................................................. A61B 6/00
(52) U.S. Cl. ....................................... 378/19; 378/98.8
(58) Field of Search ........................... 378/19; 250/366, 250/367, 370.11

(56) References Cited

U.S. PATENT DOCUMENTS

| | | | | |
|---|---|---|---|---|
| 5,043,582 A | * | 8/1991 | Cox et al. | 250/370.09 |
| 5,464,984 A | * | 11/1995 | Cox et al. | 250/370.11 |
| 5,477,075 A | | 12/1995 | Forrest et al. | |
| 5,592,523 A | * | 1/1997 | Tuy et al. | 378/19 |
| 5,801,430 A | | 9/1998 | Forrest et al. | |
| 6,025,585 A | | 2/2000 | Holland | |

OTHER PUBLICATIONS

Development of Low Noise, Back–Side Illuminated Silicon Photodiode Arrays—S.E. Holland, et al., Lawrence Berkeley National Laboratory, University of California, Berkeley, California.

* cited by examiner

Primary Examiner—Robert H. Kim
Assistant Examiner—Jurie Yun
(74) Attorney, Agent, or Firm—Fay, Sharpe, Fagan, Minnich & McKee, LLP

(57) ABSTRACT

A CT scanner (10) includes a reconstruction processor (32) for reconstructing an image from digital signals from detector arrays (20). Each detector array includes scintillation crystals (22) arranged in an array for converting x-ray radiation into light. An array of back-illuminated photo diodes (24) is mounted beneath the scintillation crystal array for converting the light emitted from the scintillation crystals into electrical charge. The electrical charge from the back-illuminated photodiodes is transmitted via a path orthogonal to the detector array (20, 40) to signal processing circuitry (66). The back-illuminated photodiode has a back-side (26) which is in optical communication with the crystal array (22) and which is optically transmissive to photons of light emanating from the crystal. The converted electrical charge leaves the photodiode via electrical connections (28) or bump bonds (62, 72) on the front side of the photodiode. This arrangement allows a plurality of paths (46) through the substrate (42, 64) supporting the photodiode to provide electrical connectivity (44) from the array to processing circuitry (66), reducing or eliminating the bottleneck of electrical leads from conventional arrays.

23 Claims, 8 Drawing Sheets

BACK-ILLUMINATED PHOTODIODES FOR COMPUTED TOMOGRAPHY DETECTORS

BACKGROUND OF THE INVENTION

The present application relates to the art of medical diagnostic imaging in which penetrating radiation is received by radiation sensitive detectors. The application subject matter finds particular use in computerized tomographic (CT) scanners and will be described with particular reference thereto. However, the invention may also find use in connection with other diagnostic imaging modalities, industrial quality assurance imaging, airport baggage inspection, x-ray fluoroscopy and the like.

Modern x-ray computer tomography scanners commonly employ several hundred x-ray detectors to convert x-ray energy into electrical signals. A detector is usually composed of a scintillator to convert x-ray energy into light and a photodiode to convert that light into an electrical current. The formats of photodiodes used in CT applications can range from a single element, 1-D arrays to a multi-element 2-D arrays.

The electrical signal from each active photodiode element is individually routed to an adjacent pre-amplifier channel. A wire bond connects a top surface bond pad on one end of the photodiode to an external connection. The conductive path to the electronics is completed using various design options. Pre-amplifiers are either located on the same PC board that includes the detector array or at a more distant location accessed by a cable.

The bond pads are typically located at one end of the photodiodes in sparse 1-D arrays. As the density of elements in the array increases, the bond pads are located on either end of the 1-D array. In still higher density arrays, the wire bonds in adjacent channels are made at alternate ends.

The wire bond density becomes even more acute for 2-D arrays. A conductive trace from each inner photodiode element in a 2-D array must be connected to the "outside world". This trace is usually included on the photodiode surface between rows of active photodiode elements. One trace is required per element and each trace usually terminates in a bond pad at an end of the 2-D array. Wire bonds from each trace are then made to external connections.

As the number of elements in a 2-D array gets large, two restrictions occur. The space required to provide room for the conductive paths between the detector rows increases and the density of the bond pads at either end of each 2-D array also increases. There is a physical limit, both in cost, function and reliability, as to the number and size of traces and bond pads that can be made using top surface contacts. A conductive path "bottleneck" occurs if there is not enough space on a surface to accommodate the number of traces from the photodiode bond pads to the detector electronics.

Another problem relates to degradation of the signals as they travel over the long bus system between the radiation detectors and the signal processing circuitry.

CT scanners operate in a sea of extraneous radio frequency electromagnetic signals, the frequencies of which vary over a wide band. Sources of extraneous signals include nearby operating electrical components, equipment, signals from other detectors, and the like. The long bus systems include long lead wires which inadvertently act as antennas in picking up extraneous electromagnetic signals and converting them into analog signals. The extraneous analog signals are superimposed on and mix with the analog signals from the detectors. The superimposed extraneous signals appear as noise and fictitious data when reconstructed into images. The resulting images are degraded by noise, ghosting, and other artifacts.

The present invention contemplates an improved method and apparatus which overcomes the above-referenced problems and others.

SUMMARY OF THE INVENTION

In one embodiment of the present invention, a computerized tomography imaging scanner includes a radiation sensitive detector array for converting received radiation into electrical signals. An image reconstruction processor receives the signals and reconstructs images based on the received radiation for video processing and display. The detector array includes a plurality of scintillation crystals arranged in an array where each scintillation crystal converts radiation into visible light. A plurality of back-contact photodiodes is also provided arranged in an array optically coupled with the scintillation array, and electrically coupled to the signal processing circuitry.

In accordance with another aspect of the present invention, each photodiode includes an electrical lead for communicating the electrical signals, and the detector array further includes a substrate connected on a first side to the photodiode array. The substrate is configured to provide a path on other than the first side for electrical communication between the electrical lead and processing circuitry.

In accordance with another aspect of the present invention, the electrical lead from the photodiode comprises a bump bond.

In accordance with another embodiment of the present invention, an imaging system includes an x-ray radiation source which selectively illuminates a plurality of radiation detector arrays. Each radiation detector array includes a plurality of photodetectors arranged in an array and a scintillation crystal overlaying the photodetector array for converting received x-ray radiation into visible light. The array further includes a plurality of paths below the photodetector array through a substrate providing electrical connectivity between the photodetectors and signal processing circuitry.

In accordance with another embodiment of the present invention, a method includes illuminating a radiation sensitive surface with x-rays and converting the received x-rays into light. An electrical signal proportional to the light is produced and communicated to processing circuitry via a path orthogonal to the radiation sensitive surface.

In accordance with another embodiment of the present invention, a radiation detector array includes a radiation sensitive surface which converts x-ray photons into photons of light. A photoelectric device in optical communication with the radiation sensitive surface generates electrical signals responsive to the photons generated. A first substrate supports the photoelectric device and is configured to provide an electrical path from contacts on a side of the photoelectric device opposite the radiation sensitive surface through the substrate.

One advantage of the present invention resides in locating the electrical conductors from the photodiode beneath the photodiode array.

Another advantage in one embodiment of the invention resides in freeing the light sensitive surface from electrical conductors.

Another advantage of the present invention resides in the ability to disperse a plurality of electrical leads or traces through a multi-level substrate.

Another advantage in one embodiment of the invention is that the present invention increases the active surface area of the photodiodes available to receive x-rays.

Another advantage is that it improves x-ray conversion efficiency.

Yet another advantage of the present invention resides in the ability to group a plurality of detector arrays together into a variety of configurations.

Still further advantages will become apparent to those of ordinary skill in the art upon reading and understanding the following detailed description.

BRIEF DESCRIPTION OF THE DRAWINGS

The invention may take form in various components and arrangements of components and in various steps and arrangements of steps. The figures are only for purposes of illustrating preferred embodiments and are not to be construed as limiting the invention.

DETAILED DESCRIPTION OF THE PREFERRED EMBODIMENT

Figure 1:
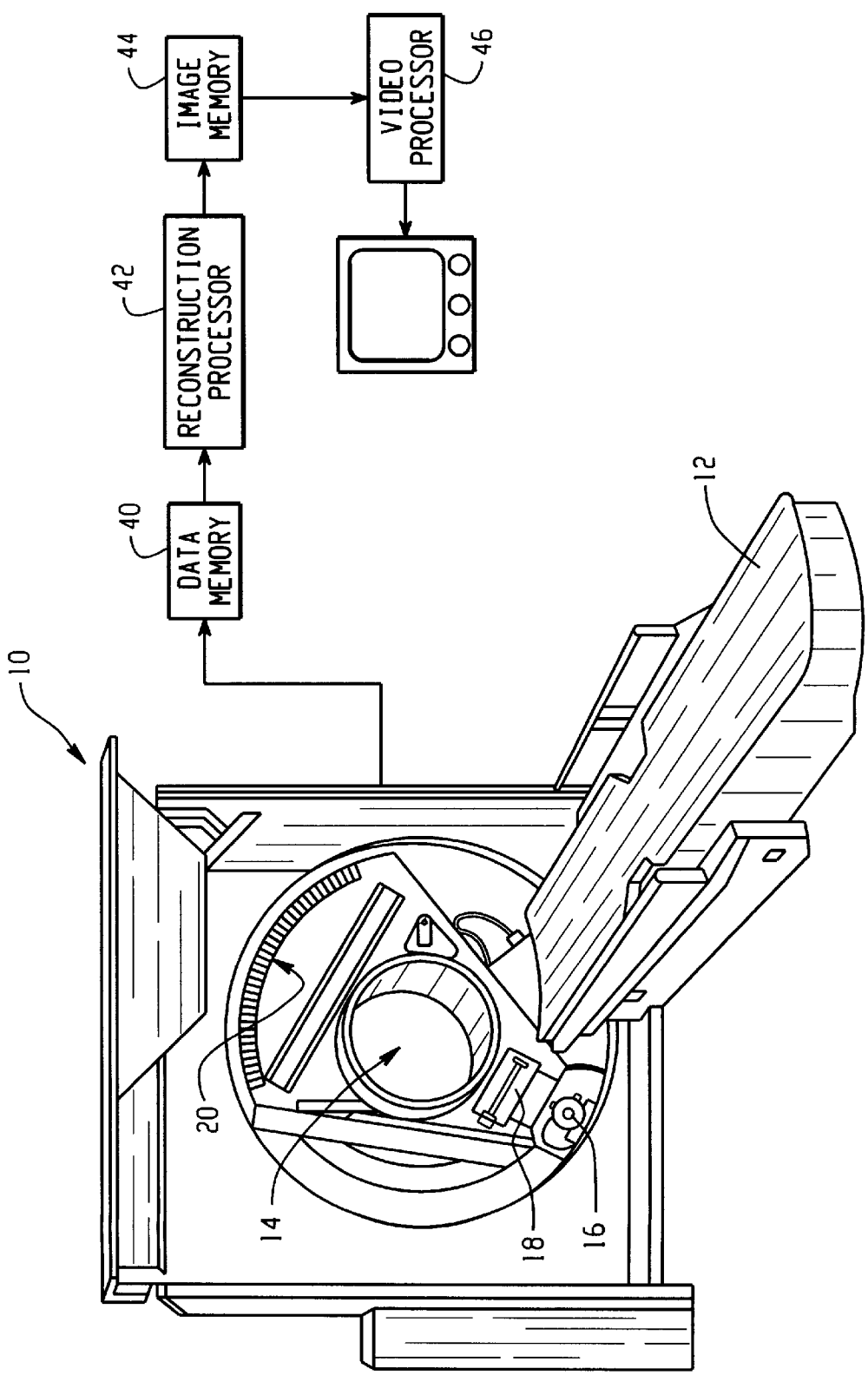
FIG. 1 illustrates a CT scanner employing a two-dimensional detector array in accordance with of the present invention.

With reference to FIG. 1, a CT scanner 10 selectively images regions of a patient supported by a patient table 12 in a scan circle or examination region 14. The patient table is positionable longitudinally. The CT scanner has an x-ray tube 16 which emits a beam of x-rays toward an area of the patient being examined. In the preferred embodiment, a collimator 18 collimates the x-rays into a cone beam. When the examination area is irradiated with the x-ray energy, a percentage of the x-rays reaching the examination area is absorbed by the patient's body. The amount of absorption depends on the density of bone or tissue upon which the x-rays are incident. The x-ray energy of the x-rays exiting the patient's body along each ray represents a linear integration of the radiation absorption of each incremental patient element along the ray. The absorption is indicative of relative tissue and skeletal densities.

With continued reference to FIG. 1, a detector array 20 receives radiation which has traversed the examination area 14. In the illustrated embodiment, the array 20 is mounted to the rotatable portion of the gantry so that it rotates along with the x-ray source 16. The segments comprising the array 20 are arranged to receive a circular cross-sectioned cone of radiation. Alternately, the array segments can be arranged to match a rectangular cone of radiation. Each array segment is disposed along a plane normal to the center line of the cone shaped x-ray beam. Cone shaped beams allow a larger volumetric region of the patient to be imaged per unit of time when compared with a patient region imaged using conventional fan shaped beams. Of course, the detectors can be manufactured in a single large array without dividing the array into segments.

Figure 2:
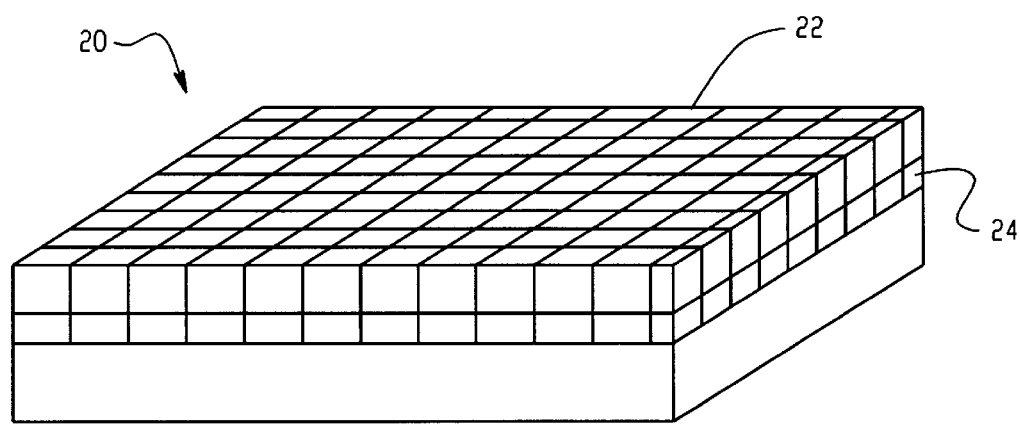
FIG. 2 illustrates a photo detector array as employed in the present invention.

With reference to FIG. 2, each segment of the detector array 20 includes an n×m array of scintillation crystals 22 and photodetectors 24 connected or preferably integrated into an integrated circuit. The scintillation crystal photodetector array is covered with a light reflective surface and a light opaque, x-ray transmissive covering (not shown) to prevent extraneous light from reaching the crystals or photodetectors. The scintillation crystal and photodetector arrays are preferably fully integrated with the integrated circuit using conventional solid-state component manufacturing techniques. However, description will further be made with respect to the electrical path from the photodetectors to signal processing circuitry.

The scintillation crystals 22 are formed from cadmium tungstate or other similar materials capable of generating visible light with a spectral match to the photodetectors upon being excited with x-ray radiation. An exemplary embodiment uses 16×16 array segments of scintillation crystals each 1 mm square area. It should be understood that a greater or lesser number of scintillation crystals of varying widths can also be employed without departing from the inventive concept of the present application. Each scintillation crystal of the 16×16 array is optically coupled to one of the photodetectors 16×16 array of photodetectors using conventional optical coupling cement, or the like.

Figure 3:
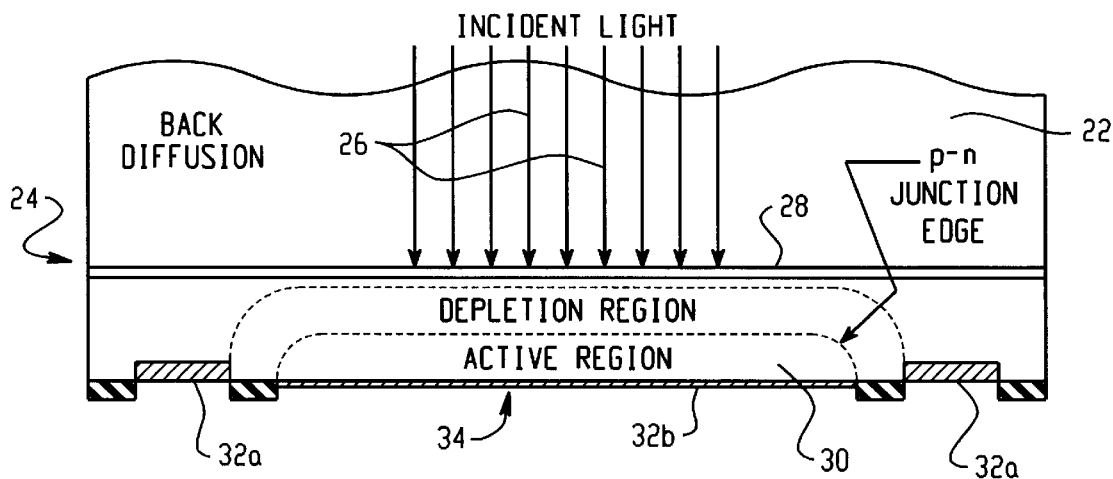
FIG. 3 illustrates a partial cross sectional view of a back-illuminated photo-diode.

Referring now to FIG. 3, x-rays that have traversed the examination area 14 (FIG. 1) are received by the scintillation crystal 22. The scintillation crystal converts these x-rays into photons of light 26. The photons of light then enter a front side 28 of one of the photodetectors 24. The scintillation crystals are covered on surfaces except the surface which is optically coupled to the photodetector with an x-ray transmissive, optical light reflective coating (not shown). Preferably, the coating is reflective such that substantially all generated light is reflected to the photodetector 24. Spatial intensity patterns of light emitted from the scintillation crystal array are proportional to spatial patterns of the x-ray radiation having traversed the examination area.

One of the scintillation crystals is mounted on a photo-detector of the 16×16 array of photodetectors to convert the light emitted from the scintillation crystal into discrete electrical charges. Again, the exemplary embodiment uses a 16×16 array of photodetectors of one square millimeter area each. It should be understood that other numbers of photodetectors and scintillation crystals can be used. The technology of forming a 16×16 array of photodetectors is readily available. For example, photodetectors in the form of photodiodes are generally manufactured from silicon wafers to by conventional masking, evaporation, etching and diffusion processes.

The light is converted by the photodetector 24 into a corresponding charge value. In a photodiode, photons of light create charge pairs in an active area 30. The charge is carried from the active area 30 to a substrate via electrical leads or connectors 32a, 32b on the backside 34 of the device as an output current that is proportional to the number of light photons received.

Figure 4:
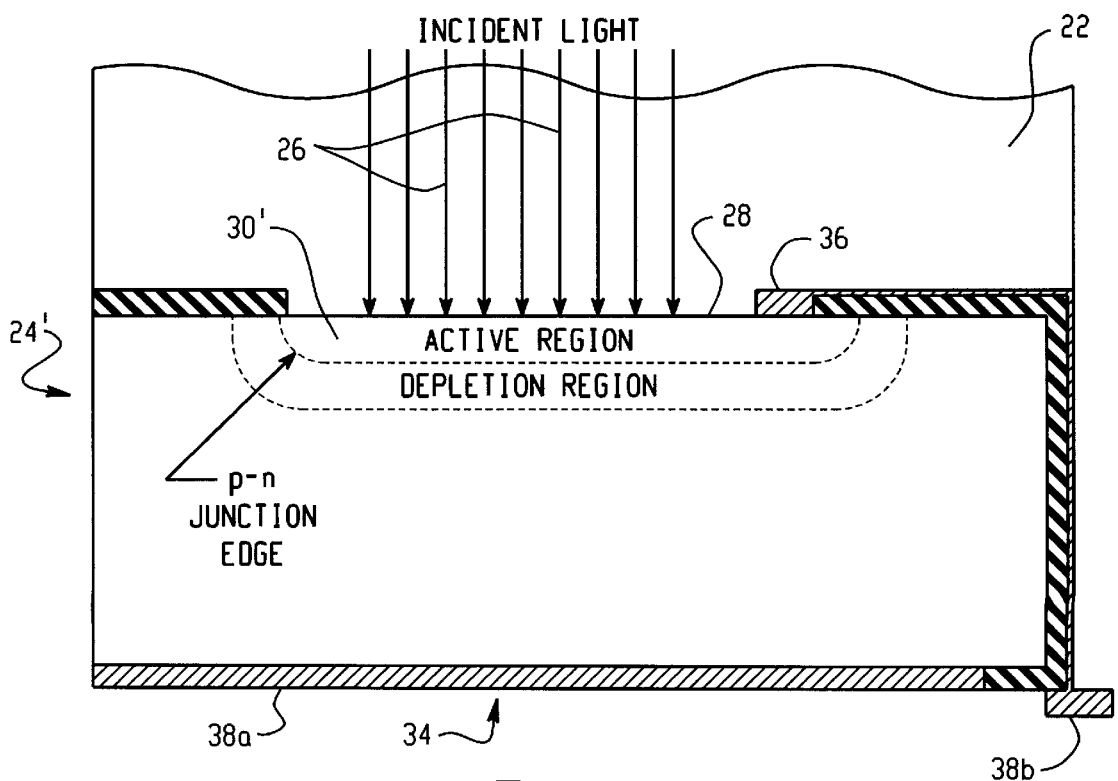
FIG. 4 illustrates a partial cross sectional view of a modified conventional photodiode.

With reference now to FIG. 4, an alternate embodiment employs a front illuminated or conventional photodiode 24' modified to provide electrical connectivity between a front contact 36 and a backside contact 38b at the backside 34 of the photodetector 24'. It can now be appreciated that numerous options are available to electrically connect the front side contact 36 to the backside contact 38b such as the external connection illustrated, an insulated connection through the silicon itself and the like.

Referring back to FIG. 1, the photodetector array 20 is in electrical communication (more thoroughly discussed below) with a data memory 40 for receiving signals indicative of the received radiation. The memory 40, is accessible by a reconstruction processor 42 which converts the scintillation events into a diagnostic image using convention reconstruction algorithms. The image is stored in image memory 44 and is selectively accessible and displayable through a video processor 46.

Conventionally, however, traces or electrical paths can only be brought out from either side of the photodiode arrays. This limitation tends to cause a conductive trace "bottleneck" on the surface of the substrate when the number of detectors per unit area becomes very large. Desirably, this limitation is not imposed by the back-illuminated photodiode design since all connections to the 'outside world' are made through the underside of the silicon chip. As an example, if electrically conductive contacts on a photodiode array, inverted by 180 degrees, are bump bonded to a mating contact on a substrate, the connection "bottleneck" can be eliminated. Electrical connections to the electronics are made through multi-layered conductors that are located under the photodiode array, rather than wire bonded contacts on a single surface adjacent to the array. The number of the back-illuminated photodiode arrays that are tiled together is unrestricted as long as the spatial placement requirements, imposed by the scanner design, are met. In fact a myriad of possible 'sub' back-illuminated photodiode configurations could make up a larger array. The choice of size and configuration of sub-arrays is a matter of function and cost.

For the sake of simplicity in further describing many of the following figures, some necessary details are omitted, such as analog common or ground connections required for proper operation. However, these details are readily apparent to those skilled in the art. Moreover, instances of back-illuminated photodiodes below can be substituted with the modified conventional photodiode as noted above where the contacts are made on the backside of the photodiode.

Figure 5:
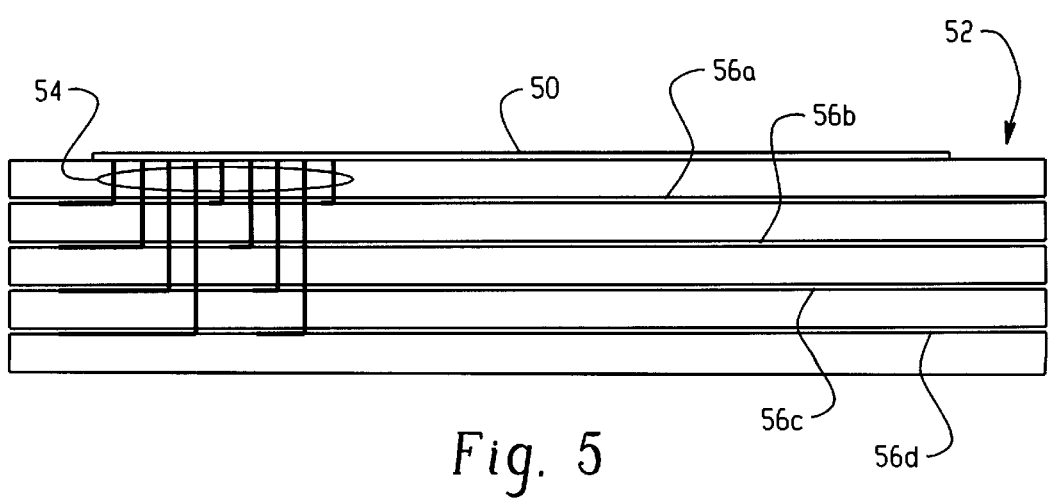
FIG. 5 is a cross sectional view of a photodetector array and multi-layer substrate.

Referring now to FIG. 5, a back-illuminated photodiode (BIP) 2-D array 50 is used to make 2-D connections through a substrate 52. The constraints imposed by the 1-D or surface connection PCB surface 'bottleneck' are relieved by making connections on the underside of the photodiode 50 through the substrate 52. Typically, bump bonds provide electrical contact from the BIP 50 to a matching contact on the surface of substrate 52. Vias 54 in the substrate, in turn, electrically interconnect the top surface contacts with internal conductive traces 56a–56d in different layers in the multi-layer substrate 52. The conductive traces 56 in the multi-layer substrate interconnect with processing chips (not shown) elsewhere. It is the parallelism of these several conductive layers and traces 56 that 'breaks the bottleneck'.

Figure 6:
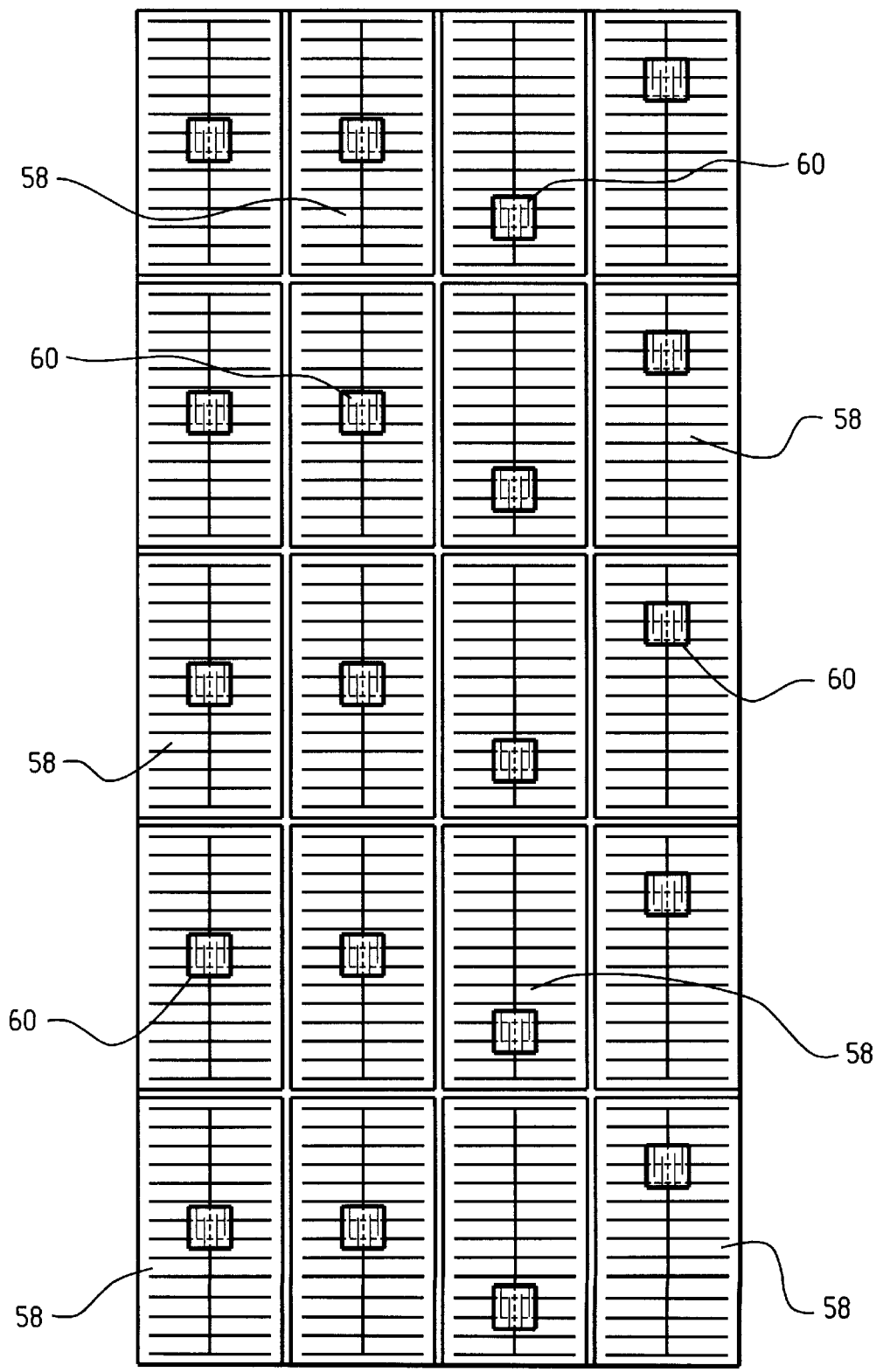
FIG. 6 is a plan-form view of a detector array incorporating a fish-bone anode structure.

A back-illuminated photodiode array 58 with a 'fishbone' arrangement of anode pads 60, shown in FIG. 6, allows more design freedom in the placement of the anode pads 60. A BIP with a "fishbone anode" has less capacitance than a BIP with a conventional fully diffused anode structure.

Figure 7:
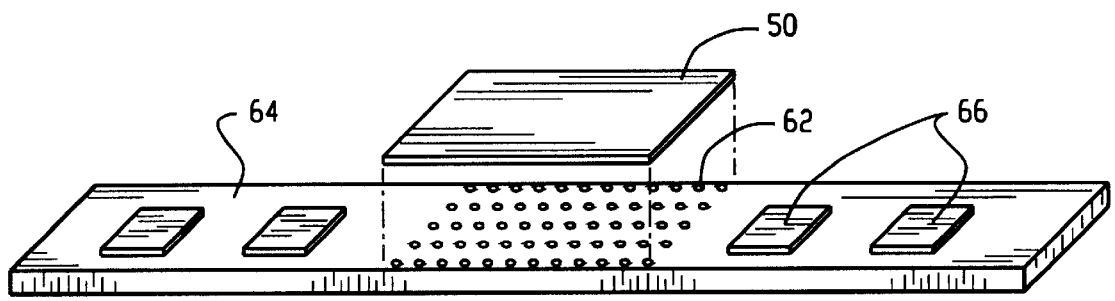
FIG. 7 is an exploded perspective view of a photodetector bump bonded to a substrate.

FIG. 7 is an exploded illustration of a 2-D BIP 50 bump bonded 62 directly to a daughter board 64 which also carries detector electronics 66. The electrical charge is amplified and converted to a voltage in the preamplifier. Additionally, the electronics 66 will subtract the amplifier offset digitized the signal value.

Figure 8:
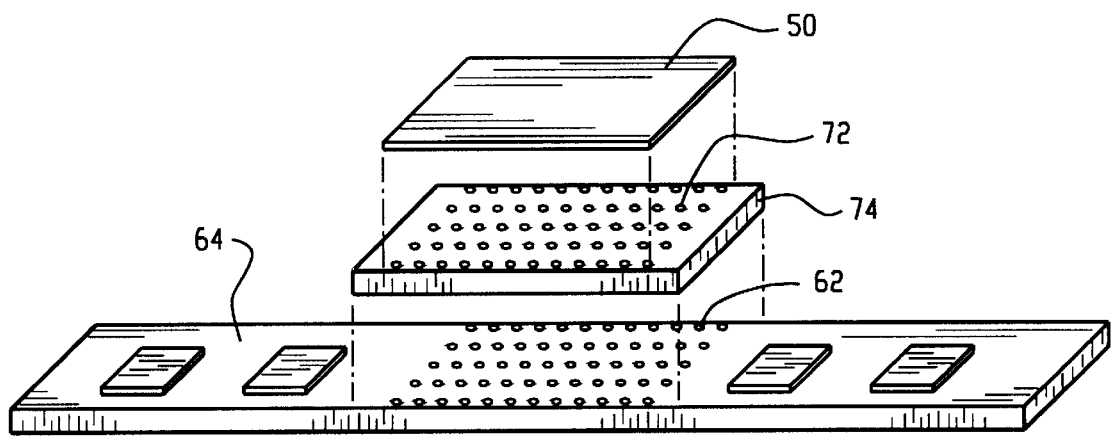
FIG. 8 is an exploded perspective view of an alternate embodiment of a detector bump bonded to an intermediate substrate which is in turn bump bonded to a daughterboard.

FIG. 8 is an exploded illustration of a 2-D BIP 50 bump bonded 72 to a substrate 74 that, in turn, is bump bonded 62 to the daughter board 64 with the detector electronics.

Figure 9:
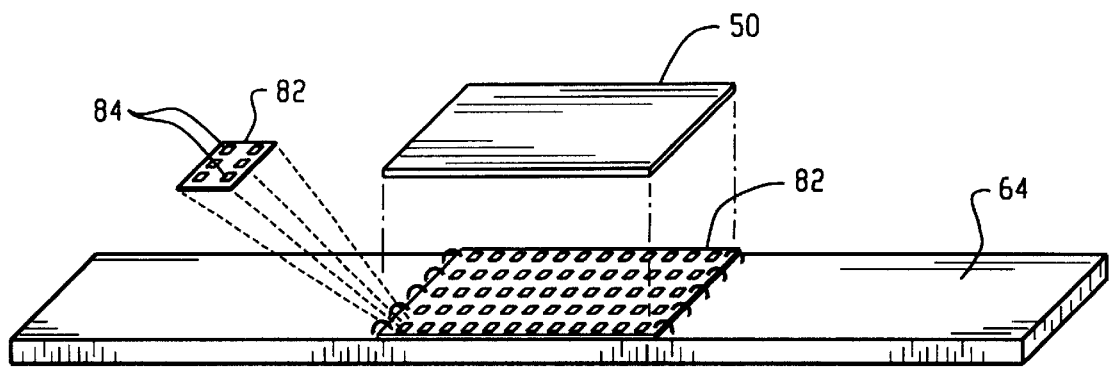
FIG. 9 is an exploded perspective view of an alternate embodiment of a photodetector bump bonded to a silicon chip bearing individual integrated circuits.

As best illustrated in FIG. 9, chip-on-board technology allows the integration of miniaturized electronics on a single condensed area. A BIP 50 is bump bonded to a silicon chip 82 bearing the integrated ASICs 84.

In the illustrated embodiment the BIP array 50 is a single silicon chip and the electronics 84 lie on a single separate wafer piece. Bump bonds between the BIP 50 and the silicon chip 82 are made on the die. The output and control signals come out at the ends of the electronics wafers. Each electronics channel contains current to frequency conversion and associated digital electronic circuity using CMOS technology. The assembled electronic wafer can then be mounted on a daughterboard.

Those skilled in the art recognize that the BIP alternately may be bump bonded to a silicon chip bearing the integrated chip-on-board ASICs which is then connected to the daughter board via wire bonds or bump bonds.

When mounting the BIPs through an intermediate substrate, The BIP array is a single silicon chip. The electronics preferably lie on a single separate wafer piece married to the BIP by bump bonding to a separate substrate (BIPs on top). The bump bonds on the silicon chip are made on the die. As above, the electronics channel contains current to frequency conversion and associated digital electronic circuitry using CMOS technology. The assembled electronic wafer can then be mounted on the daughterboard.

In a mosaic scheme, the BIP array consists of sub elements. The electronics are single multi-channel ASICs bonded to the bottom of a larger substrate carrier. The carrier has the dimensions of final array configuration. The BIP segments are bump bonded to top side of the carrier in a mosaic structure. The substrate is designed to accept various configurations of BIP sub-elements such as, but not limited to: 16×16, 16×32, and 16×64. The control and output signals come out at the ends of the carrier substrate.

Figure 10:
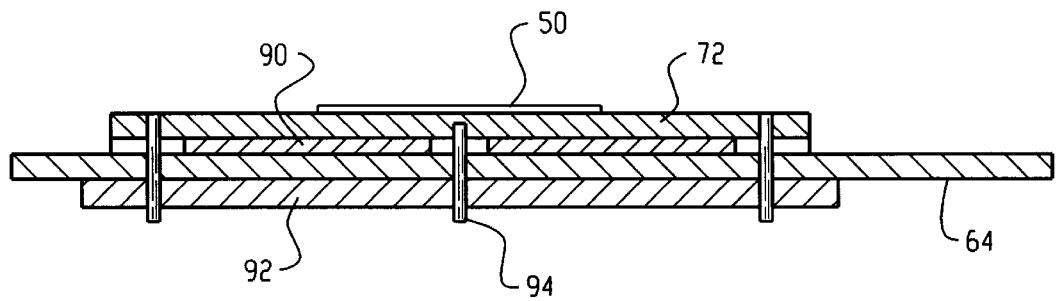
FIG. 10 is a cross sectional view of a photodetector array arranged with a spacer, a daughterboard, and a stiffening member.

In an alternate embodiment illustrated in FIG. 10, electrical contact is made from connections on the substrate to matching contacts on the daughter board via a standard commercially available elastomer connector. (Other similar connectors could also be used.) FIG. 10 illustrates an arrangement of a substrate 72 bearing the BIP 50, a spacer 90, a daughterboard 64 and a stiffening member 92. The spacer 90 provides spatial alignment between the daughterboard 64 and the daughterboard and also controls the compression of the elastomer. The stiffener 92 keeps the assembly flat and also provides a surface to which fasteners can be anchored. A central stud fastener 94 does not go through the substrate 72. One or two layers of the substrate are not penetrated to assure continuity of the top central BIP connections to the underside connections.

Figure 11:
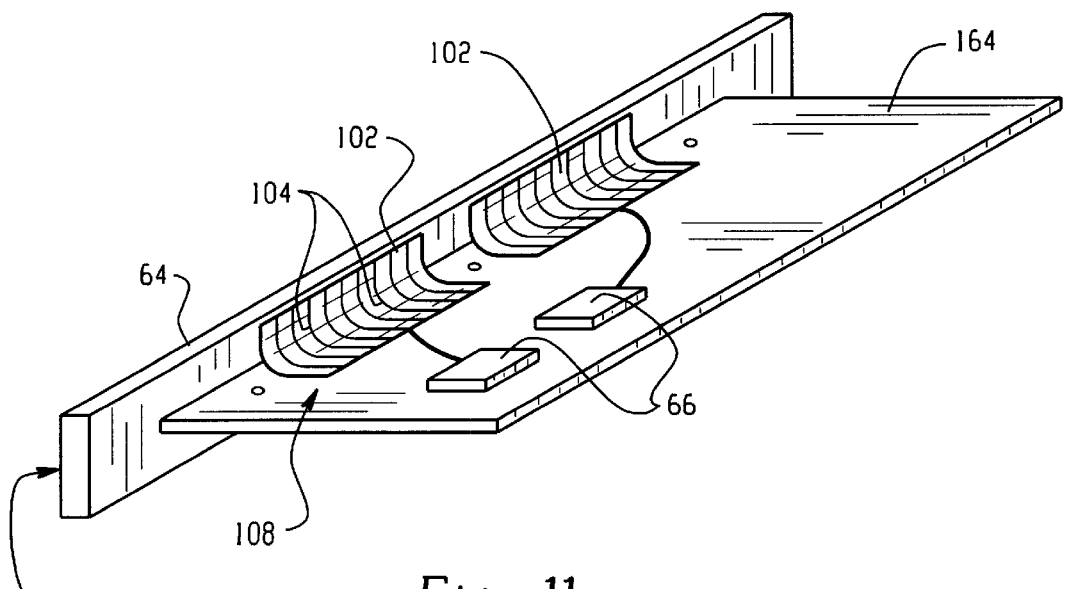
FIG. 11 is a perspective view of an alternate embodiment linking processing circuitry to the detector array in a "T" configuration.

In another embodiment illustrated in FIG. 11, the BIP 50 is mounted to a first substrate 64 and detector electronics 66 are on a board 164 out of plane from substrate 64 but electrically linked to the substrate 64 and the BIP 40 via a 'wire skin' 102. Wires 104 on one end of the 'wire skin' 102 are aligned and soldered to contacts on the underside of the substrate 64. The wires on the opposite end are aligned and make physical and electrical connection to outboard mating contacts 108. The 'wire skin' 102 illustrated is bent to a ninety degree angle. The illustrated gap between the 'wire skins' 102 is included for convenience of assembly but is not a requirement.

Figure 12:
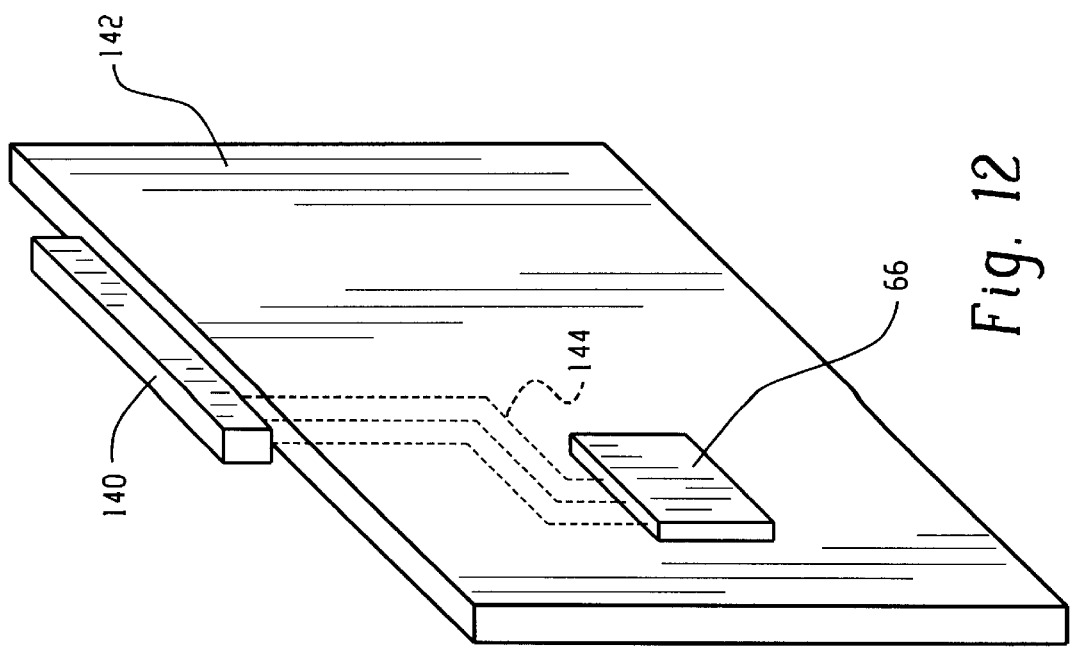
FIG. 12 is a perspective view of a one-dimensional array mounted onto the edge of a substrate.

Alternately, as illustrated by FIG. 12 a 1-D scintillation crystal and BIP array 140 is mounted on the edge of a PCB or ceramic substrate 142. The conductive signal traces of one layer of the PCB terminate at the edge of the board and are gold plated. Internal traces 144 are routed to the inputs of an ASIC 66. Those skilled in the art can now appreciate that the concept is expandable to a 2×N, 4×N or M×N array.

Figure 13:
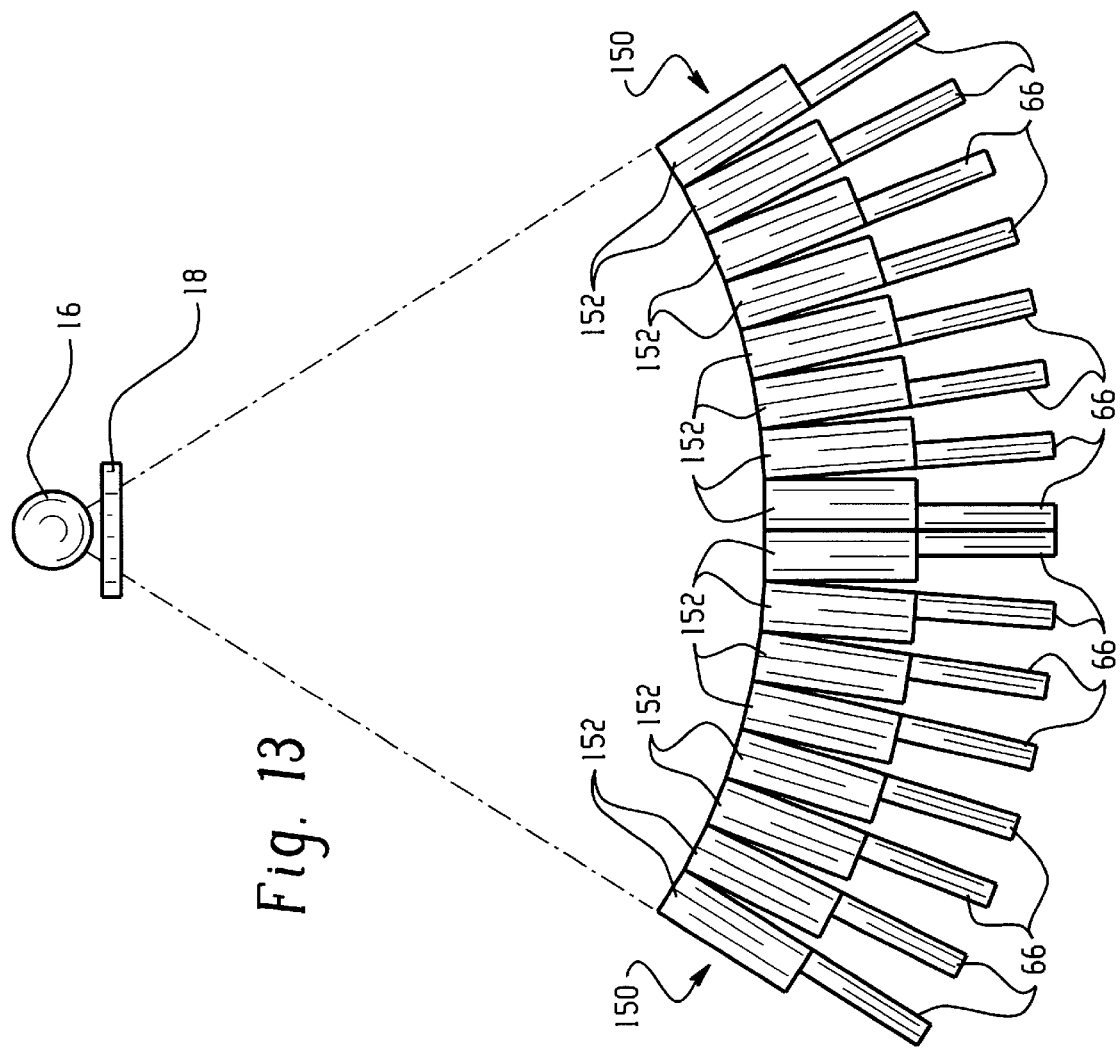
FIG. 13 is a simplified depiction of a packaging concept allowing construction of nested detectors in an arc configuration.

FIG. 13 illustrates an embodiment of the present invention employing a radiation source 16 passing radiation through a collimator 18 onto a plurality of discrete detector arrays 150. The illustrated arrays 150 are an alternate embodiment of the configuration shown in FIG. 12, although it is apparent that the configuration shown in FIG. 11 or 12 can be employed with no loss of functionality. Reference to FIG. 13 reveals that the arrays 150 are disposed adjacent to one another such that the respective radiation sensitive surfaces or scintillation crystals 152 abut neighboring crystal arrays 152. It can now be appreciated that even larger arrays are possible employing principles of the present invention by disposing arrays not only side to side as illustrated but also end to end (along a longitudinal axis through the examination area).

Figure 14:
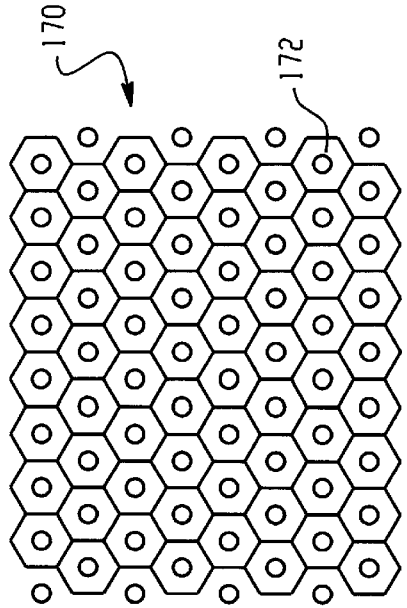
FIG. 14 is a plan form view of an alternate photodetector array arranged with high density very small elements; and, FIG. 15 is a perspective view of a plurality of arrays tiled to form a larger array.

Reference to FIG. 14 illustrates another embodiment in which an array 170 is configured from high density, very small elements 172. This BIP array 170 can accommodate a number of application specific embodiments. The dimensions of a scintillator array and substrate contacts can be optionally matched in size and aligned to achieve the desired spatial response. The array 170 can accommodate various configurations saving the cost of creating masks for the separate embodiments.

In general, the spatial resolution of a radiation imaging detector is a function of the spatial resolution of the radiation converter and the spatial resolution of the photodiode. The spatial resolution of a back-illuminated photodiode is a function of the density and distribution of the charge collection anodes (see e.g. FIG. 6). A back-illuminated photodiode can be configured with a dense matrix of closely spaced anodes. With each of these anodes electrically connected to readout electronics the spatial resolution is high and dependent on their density and spatial distribution. Spatial resolution is generally limited by the spreading of the electrons as they traverse through the silicon. The spatial resolution increases as the silicon thickness decreases.

The size and spatial distribution of the mating bond pads on the substrate that connect the photodiode's anodes can be designed to alter the charge collection pattern, hence spatial sensitivity of the sensor is also altered. A photodiode thus configured with a high density matrix of anode contacts can serve as a basis for more than one type of radiation sensor.

If, for example, a uniform phosphor scintillation screen is used to convert radiation into light, it is possible to connect all anodes to one common mating connection and measure one integrated response. This is inefficient but possible.

The other extreme is to connect each anode to its own readout electronics. The resolution of this configuration can be relatively high.

The compromise between total integration of all elements in the matrix and total separation of each element is to configure the substrate's bond pads to suit specific applications using the same back-illuminated photodiode. For example, each bond pad on a substrate could be electrically connected to 4 anodes with a 2 by 2 matrix or a 1×4 matrix in the "z" direction or a 1×4 matrix in the "x" direction (i.e. transverse to the "z"). It can now be appreciated that a myriad of combinations can be configured, each to suit a special application.

Figure 15:
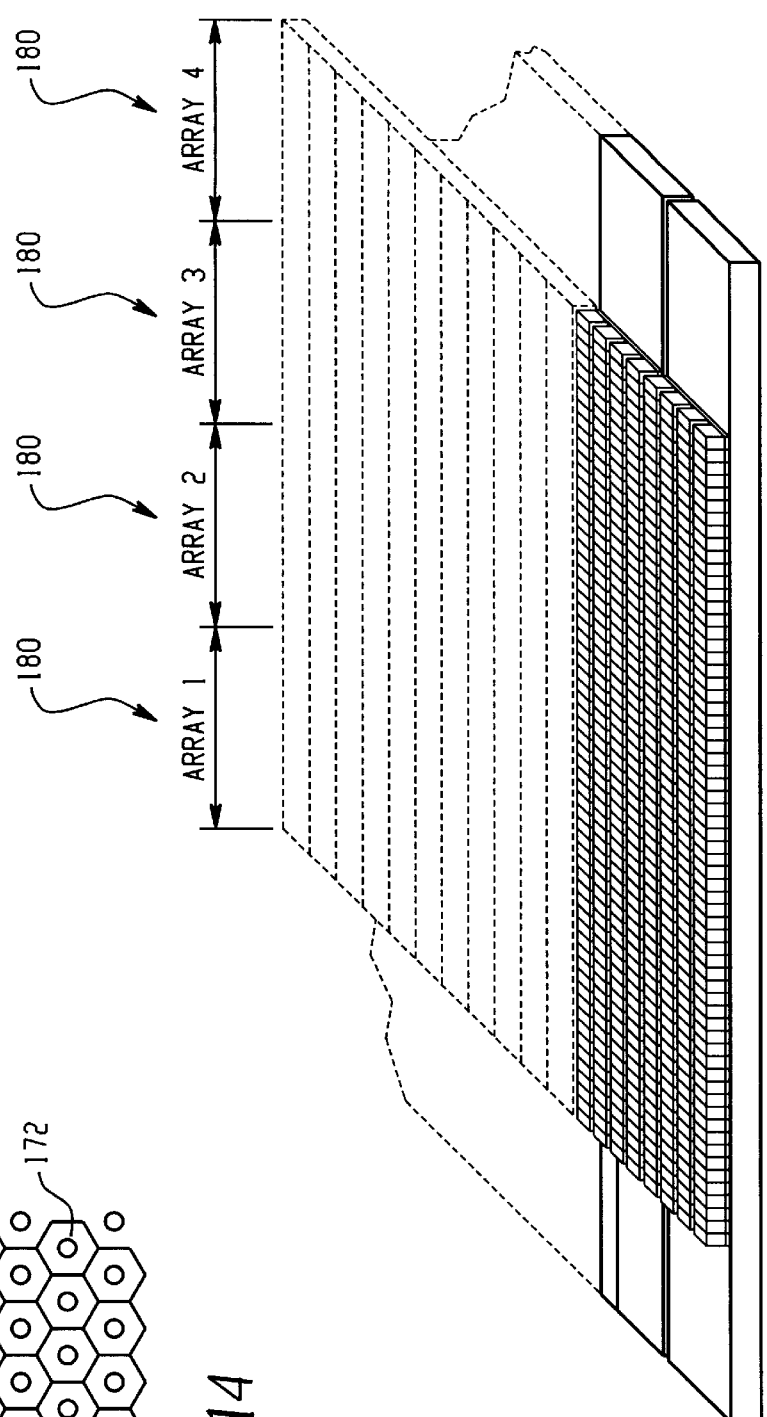

With reference now to FIG. 15, an illustration of a plurality of 2-D arrays 180 are tiled closely together due to the electrical connections on the back side of the packages. This desirably allows designers to arrange much larger arrays having complete detector coverage in an area of interest. Moreover, arrays in a variety of shapes are also possible using principles of the present invention. In some embodiments, the ASIC's or electronics can be similarly tiled and/or located on either side of the substrate. This flexibility permits placement of the electronics outside of an area of radiation.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. In a computerized tomography imaging scanner including a radiation sensitive detector array for converting received radiation into electrical signals, and an image reconstruction processor for reconstructing images based on the received radiation, the detector array comprising:

a plurality of scintillation crystals arranged in an array, each of said scintillation crystals converting radiation into visible light;

a plurality of back contact photodiodes arranged in an array optically coupled with the scintillation crystal array; and a multi-layer substrate on which the photodiode array is arranged, the substrate having a plurality of is electrical conductor traces spatially distributed through the multi-layer substrate, the traces electrically connected directly to the photodiode contacts arranged distal from the scintillation crystals.

2. The computerized tomography imaging scanner as set forth in claim 1, further comprising:

solder bump bonds that connect the photodiode contacts with electrical conductor trace vias.

3. The computerized tomography imaging scanner as set forth in claim 1, further comprising:

a daughterboard on which the substrate is arranged, the daughterboard further having detector electronics arranged thereon which are in electrical communication with the array of photodiodes via the conductor traces.

4. The computerized tomography imaging scanner as set forth in claim 3, wherein the substrate is arranged on an edge of the daughterboard.

5. The computerized tomography imaging scanner as set forth in claim 3, wherein the substrate further comprises:
   a plurality of substrates that are tiled closely together on the daughterboard to form a detector array having a selected shape.

6. A computerized tomography imaging scanner including a radiation sensitive detector array for converting received radiation into electrical signals, and an image reconstruction processor for reconstructing images based on the received radiation, the detector array comprising:
   a scintillation crystal array that receives the radiation and converts at least a portion of the radiation into visible light;
   a photodiode array optically coupled with the scintillation crystal array; and
   electronic detector circuitry arranged on a substrate disposed out of a trajectory of the radiation received by the scintillation crystal array.

7. An imaging system comprising:
   an x-ray radiation source selectively generating a beam of x-ray radiation to traverse an examination region from a multiplicity of directions; and
   a radiation detector array positioned opposite the examination region from the radiation source to receive x-ray radiation that has traversed the examination region, the radiation detector array including:
      a plurality of photodetectors arranged in an array,
      a scintillation crystal overlaying the photodetector array for converting received x-ray radiation into visible light, the scintillation crystals being optically coupled to the photodetectors, and
      a plurality of paths below the photodetector array through a substrate, the paths providing electrical connectivity between the photodetectors and signal processing circuitry, the paths defining two spatial planes, the first spatial plane arranged parallel to the photodetector array, and the second spatial plane arranged angularly offset from the first spatial plane.

8. The imaging system as set forth in claim 7, where the plurality of photodetectors each include a photodiode having a front side adjacent to the scintillation crystal for receiving incident light and a backside to which electrical connections are affixed.

9. The imaging system as set forth in claim 8, wherein the substrate has a first portion corresponding to the first spatial plane that lies parallel to and is comparably sized to the photodetector array.

10. The imaging system as set forth in claim 7, wherein portions of the paths through the substrate are orthogonally disposed relative to the photodetector array.

11. The imaging system as set forth in claim 7, wherein the radiation detector array converts radiation into electrical imaging signals, the system further comprising:
   an image reconstruction processor in data communication with the signal processing circuitry for reconstructing the imaging signals into images representative of radiation transmissive properties of a subject in the examination region.

12. The imaging system as set forth in claim 7, wherein the beam of x-ray radiation forms a cone-shaped beam and the array of radiation detector arrays is sized to a transverse cross-section of the cone beam.

13. An imaging system including an x-ray radiation source selectively generating a beam of x-ray radiation that traverses an examination region from a multiplicity of directions, and a radiation detector array positioned opposite the examination region from the radiation source, the radiation detector array including:
   a plurality of photodetectors arranged in an array, each photodetector including a backside to which electrical connections are affixed;
   a scintillation crystal overlaying the photodetector array for converting received x-ray radiation into light, the scintillation crystals being optically coupled to the photodetectors;
   a substrate comprising a first substrate layer disposed parallel to the photodetector array and a second substrate layer disposed perpendicular to and in support of the first substrate layer; and
   a plurality of paths below the photodetector array through the substrate, the paths providing electrical connectivity between the photodetectors and signal processing circuitry.

14. An imaging system comprising an x-ray radiation source for transmitting x-ray radiation into an examination region, and an x-ray detector for detecting the transmitted x-ray radiation, the detector comprising:
   a plurality of scintillation crystals facing the examination region which convert at least a portion of the transmitted x-ray radiation into light;
   an array of back-illuminated photodiodes that receive the light generated by the scintillation crystals, the photodiodes having contacts disposed on a side of the photodiode distal from the scintillation crystals;
   a first planar substrate portion which supports the photodiode array, the first substrate portion defining electrical paths connected with the photodiode contacts;
   a second planar substrate portion mounted at an angle to the first planar substrate portion; and
   detector electronics arranged on the second planar portion that are electrically connected with the electrical paths of the first substrate portion.

15. A method comprising:
   illuminating a radiation sensitive surface with x-rays;
   converting the x-rays illuminating the radiation sensitive surface into light;
   producing an electrical signal proportional to the converted light; and
   communicating the electrical signal through a substrate to processing circuitry sheltered from the x-rays via a path orthogonal to the radiation sensitive surface.

16. The method as set forth in claim 15, further comprising a plurality of radiation sensitive surfaces and photodetectors arranged as an array, the method further comprising:
   associating the radiation sensitive array with the photodetector array;
   mounting the photodetector array to the substrate such that the photodetector array lies between the radiation sensitive array and the substrate; and
   establishing electrical communication between the processing circuitry and the photodetector array.

17. The method as set forth in claim 16, wherein the x-rays illuminating the radiation sensitive surface include cone beam x-rays, and the method further comprises:

shaping the photodetector array complementarily in relation to a cross section of the cone beam.

18. A method for detecting x-rays in clinical imaging, comprising:

at a scintillator surface, converting x-rays to visible light;

detecting the visible light output with back contact photodiodes;

communicating the electrical signals generated by the back contact photodiodes to processing circuitry through back contacts of the photodiodes; and shielding the processing circuitry from the x-rays using a shielding material disposed between the back contact photodiodes and the processing circuitry.

19. A radiation detector array comprising:

a radiation sensitive surface which converts received radiation into photons of light;

a photodiode which has a front side that is free of electrical contacts in optical communication with the radiation sensitive surface, which generates electrical signals responsive to the photons of light generated by the radiation sensitive surface, and which has its signal contacts arranged on a back side opposite the front side; and a first substrate supporting the photodiode, the first substrate configured to provide an electrical path from the contacts on the back side of the photodiode through the first substrate.

20. The radiation detector as set forth in claim 19, where the radiation detector array comprises a plurality discrete detector arrays adjacent to others of the arrays such that respective radiation sensitive surfaces abut adjacent radiation sensitive surfaces.

21. A radiation detector array comprising:

a scintillator which converts received radiation into photons of light;

a photodiode which detects the photons of light, the photodiode having a front side in optical communication with the scintillator, and a back side on which signal contacts are arranged opposite the front side;

a first substrate supporting the photodiode, the first substrate providing an electrical path from the back side contacts through the first substrate;

a second substrate disposed in non-coplanar fashion relative to a plane defined by the first substrate;

an electrical connection between the electrical path through the first substrate and detector electronics mounted to the second substrate; and a radiation absorbing material disposed between the first and second substrates to shield the detector electronics from radiation exposure.

22. The radiation detector as set forth in claim 21, where the radiation detector array comprises a plurality discrete detector arrays adjacent to others of the arrays such that respective radiation sensitive surfaces abut adjacent radiation sensitive surfaces.

23. A radiation detector array comprising:

a scintillator which converts received radiation into photons of light;

a photodiode which detects the photons of light, the photodiode having a front side in optical communication with the scintillator, and a back side on which signal contacts are arranged opposite the front side;

a first substrate supporting the photodiode, the first substrate providing an electrical path from the back side contacts through the first substrate;

a second substrate disposed out of a trajectory of radiation received by the scintillator; and an electrical connection between the electrical path through the first substrate and detector electronics mounted to the second substrate.

* * * * *